United States Patent [19]

Elbe et al.

[11] 4,451,281

[45] May 29, 1984

[54] FUNGICIDAL AND PLANT GROWTH-REGULATING 1-AZOLYL-2-OXIMINOBUTANE AND USE

[75] Inventors: Hans-Ludwig Elbe; Wolfgang Krämer, both of Wuppertal; Karl H. Büchel, Burscheid; Klaus Lürssen, Bergisch-Gladbach; Paul Reinecke; Hans Scheinpflug, both of Leverkusen, all of Fed. Rep. of Germany

[73] Assignee: Bayer Aktiengesellschaft, Leverkusen, Fed. Rep. of Germany

[21] Appl. No.: 490,688

[22] Filed: May 2, 1983

[30] Foreign Application Priority Data

May 19, 1982 [DE] Fed. Rep. of Germany ....... 3219041

[51] Int. Cl.³ ..................... A01N 43/50; A01N 43/64; C07D 233/61; C07D 249/08
[52] U.S. Cl. ........................................... 71/92; 71/76; 424/264; 424/273 R; 548/262; 548/341
[58] Field of Search ................ 548/262, 341; 424/269, 424/273 R; 71/92, 76

[56] References Cited

U.S. PATENT DOCUMENTS 4,352,804  10/1982  Van Zorge ........................ 548/341

FOREIGN PATENT DOCUMENTS 2657578  7/1977  Fed. Rep. of Germany .
2723942  12/1978  Fed. Rep. of Germany .
2816817  10/1979  Fed. Rep. of Germany .

Primary Examiner—Robert W. Ramsuer
Attorney, Agent, or Firm—Sprung, Horn, Kramer & Woods

[57] ABSTRACT

1-Azolyl-2-oximinobutane derivatives of the formula $$R^2-CH_2-\underset{\underset{CH_3}{|}}{\overset{\overset{CH_3}{|}}{C}}-\underset{\underset{\underset{C-R^1}{|}}{N}}{\overset{\|}{C}}-CH_2-N\overset{\diagup=N}{\underset{\diagdown}{\diagdown}}\underset{A}{\Big|}$$

in which
A is nitrogen or CH,
R¹ is hydrogen, alkyl, halogenoalkyl, alkenyl, alkinyl, or optionally substituted benzyl, phenyl, cycloalkyl, cycloalkylalkyl or cycloalkenyl, and
R² is optionally substituted phenyl, phenoxy, phenylthio, phenylsulphinyl or phenylsulphonyl, or physiologically acceptable addition products thereof with acids or metal salts, which possess fungicidal and plant growth-regulating activities.

10 Claims, No Drawings

FUNGICIDAL AND PLANT GROWTH-REGULATING 1-AZOLYL-2-OXIMINOBUTANE AND USE

The present invention relates to new 1-azolyl-2-oximinobutane derivatives, several processes for their preparation, and their use as fungicides and plant growth regulators.

It has already been disclosed that substituted 2-azolyl-1-benzyloximino-1-phenylethanes have good fungicidal properties (compare: DE-OS (German Published Specification) No. 2,657,578, DE-OS (German Published Specification) No. 2,723,942 and U.S. Pat. No. 4,364,955). The action of these compounds, however, is not always completely satisfactory, in particular when the compounds are used in low amounts and concentrations.

New 1-azolyl-2-oximinobutane derivatives of the general formula (I)

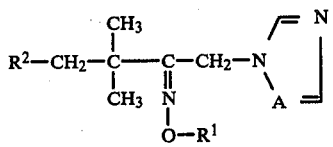

in which
A represents nitrogen or the CH group,
$R^1$ represents hydrogen, alkyl, halogenoalkyl, alkenyl, alkinyl, optionally substituted benzyl or phenyl, and cycloalkyl, cycloalkylalkyl or cycloalkenyl, each of which is optionally substituted, and
$R^2$ represents phenyl, phenoxy, phenylthio, phenylsulphinyl or phenylsulphonyl, each of which is optionally substituted,
and their physiologically acceptable acid additions salts and metal salt complexes have been found.

The compounds of the formula (I) can be in the syn form or anti form; they are predominantly obtained as mixtures of the two forms.

It has also been found that the 1-azolyl-2-oximinobutane derivatives of the formula (I) are obtained when (a) azolylketones of the formula (II)

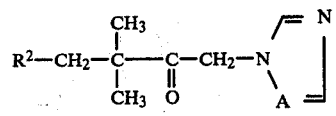

in which
A and $R^2$ have the abovementioned meaning,
are reacted with substituted hydroxylamines of the formula (III)

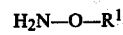

$$H_2N-O-R^1 \qquad (III)$$

in which
$R^1$ has the abovementioned meaning,
if appropriate in the presence of a diluent; or (b) the 1-azolyl-2-oximinobutane derivatives according to the invention of the general formula (Ia)

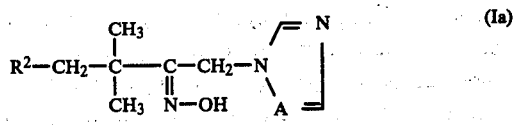

in which
A and $R^2$ have the abovementioned meaning,
are reacted with halides of the formula (IV)

$$Hal-R^1 \qquad (IV)$$

in which
$R^1$ has the abovementioned meaning and
Hal represents chlorine or bromine,
if appropriate in the presence of a strong base and in the presence of a diluent, or (c) 1-halogeno-2-oximinobutane derivatives of the general formula (V)

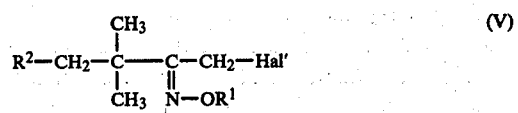

in which
$R^1$ and $R^2$ have the abovementioned meaning and
Hal' represents chlorine or bromine,
are reacted with 1,2,4-triazole or imidazole in the presence of an acid-binding agent and in the presence of a diluent.

An acid or a metal salt can, if appropriate, be added to the compounds of the formula (I) thus obtained.

Finally, it has been found that the new 1-azolyl-2-oximinobutane derivatives of the formula (I) and their acid addition salts and metal salt complexes have powerful fungicidal and plant growth regulating properties.

Surprisingly, the compounds according to the invention of the formula (I) display better fungicidal activity than substituted 2-azolyl-1-benzyloximino-1-phenylethanes known from the state of the art, which are similar compounds as regards their chemistry and action. In addition, the compounds according to the invention of the formula (I) display surprisingly good plant growth regulating action.

The materials according to the invention thus are a valuable enrichment of the art.

In addition, the compounds according to the invention of the formula (I) in which $R^1$ represents hydrogen are interesting intermediate products. Thus, acyl or carbamoyl derivatives of these compounds can be obtained in a manner which is known in principle, for example by reacting with acyl halides, isocyanates or carbamoyl chlorides.

Formula (I) gives a general definition of the 1-azolyl-2-oximinobutane derivatives according to the invention. Those compounds are preferred in which
$R^1$ represents hydrogen, straight-chain or branched alkyl having 1 to 12 carbon atoms, straight-chain or branched alkenyl or alkinyl having in each case 2 to 12 carbon atoms, straight-chain or branched halogenoalkyl having 1 to 4 carbon atoms and 1 to 5 identical or different halogen atoms, in particular chlorine and fluorine being suitable as halogen, cycloalkyl or cycloalkenyl having in each case 5 to 7 carbon atoms, cycloalkylalkyl having 3 to 7 carbon atoms in the cycloalkyl moiety and 1 to 4 carbon atoms in the alkyl moiety, benzyl or phenyl which is optionally monosubstituted or polysubstituted by identical or different substituents, the following being preferred substituents: halogen, cyano, nitro, alkyl and alkoxy having in each case 1 to 4 carbon atoms, optionally halogen-substituted phenyl or phenoxy, halogenoalkyl or halogenalkoxy having in each case 1 to 3 identical or different halogen atoms, in particular fluorine and chlorine being suitable as halogen atoms;

$R^2$ represents phenyl, phenoxy, phenylthio, phenylsulphinyl or phenylsulphonyl, each of which is optionally monosubstituted or polysubstituted by identical or different substituents, the following being mentioned as preferred substituents: halogen, nitro, cyano, furthermore alkyl, alkoxy or alkylthio having in each case 1 to 6 carbon atoms, furthermore, cyclohexyl, then halogenoalkyl, halogenoalkoxy and halogenoalkylthio having in each case 1 to 4 carbon atoms and 1 to 5 identical or different halogen atoms, in particular fluorine and chlorine being suitable as halogen, also dialkylamino having 1 to 4 carbon atoms in each alkyl moiety, then alkoxycarbonyl having 1 to 4 carbon atoms in the alkyl moiety, as well as, finally, phenyl, phenoxy, phenylthio, benzyl, benzoxy or benzylthio, each of which is optionally monosubstituted or polysubstituted by identical or different substituents, the following being mentioned as preferred substituents for the last-mentioned six groups: alkyl having 1 to 4 carbon atoms and halogen, in particular fluorine and chlorine, and A has the meaning given in the definition of the invention.

Those compounds of the formula (I) are particularly preferred in which $R^1$ represents straight-chain or branched alkyl having 1 to 8 carbon atoms, straight-chain or branched alkenyl or alkinyl having in each case 2 to 8 carbon atoms, cyclopentyl, cyclohexyl, cyclopropylmethyl, cyclopropylethyl, cyclopentylmethyl, cyclohexylmethyl, cyclohexenyl and phenyl or benzyl which is optionally monosubstituted to trisubstituted by identical or different substituents, the following being mentioned as substituents: fluorine, chlorine, bromine, cyano, nitro, methyl, ethyl, methoxy, then optionally fluorine- or chlorine-substituted phenyl or phenoxy and trifluoromethyl and trifluormethoxy, and $R^2$ represents phenyl, phenoxy, phenylthio, phenylsulphinyl or phenylsulphonyl, each of which is optionally monosubstituted or disubstituted by identical or different substituents, in particular the following being mentioned as substituents: fluorine, chlorine, methyl, as well as optionally fluorine-, chlorine- or methyl-substituted phenyl or phenoxy.

The following compounds of the formula (I) may be mentioned individually in addition to the compounds mentioned in the preparation examples (A represents not only a nitrogen atom but also the CH group)

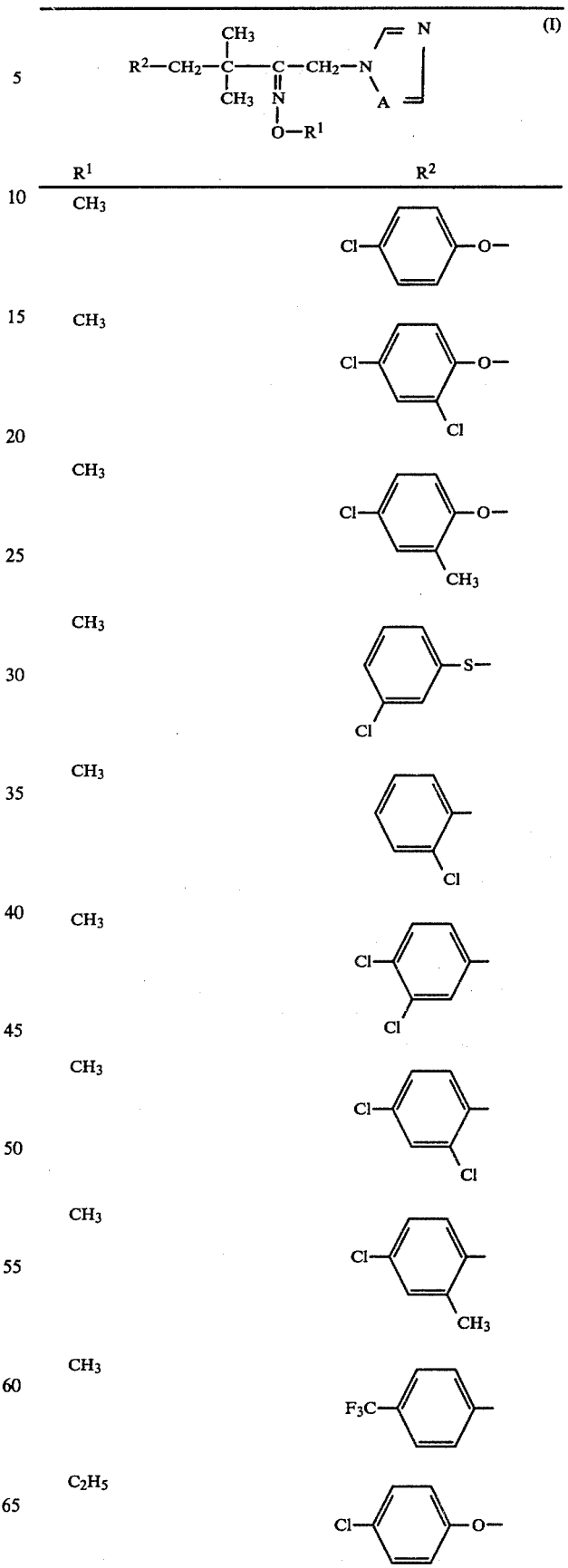

4,451,281

TABLE (continued)

Structure (I):

R²—CH₂—C(CH₃)(CH₃)—C(=N—O—R¹)—CH₂—N(—N=CH—A=CH—)  (I)

| R¹ | R² |
|---|---|
| C₂H₅ | 2,4-dichlorophenoxy (Cl at 2,4; O—) 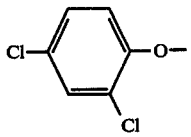 |
| C₂H₅ | 4-chloro-2-methylphenoxy 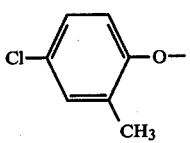 |
| C₂H₅ | 3-chlorophenylthio 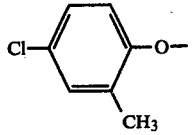 |
| C₂H₅ | 2-chlorophenyl 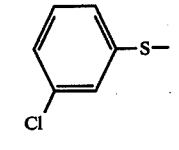 |
| C₂H₅ | 3,4-dichlorophenyl 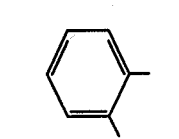 |
| C₂H₅ | 2,4-dichlorophenyl 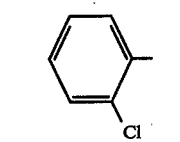 |
| C₂H₅ | 5-chloro-2-methylphenyl 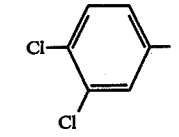 |
| C₂H₅ | 4-trifluoromethylphenyl 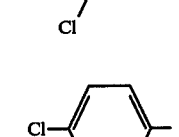 |
| n-C₃H₇ | 4-chlorophenoxy 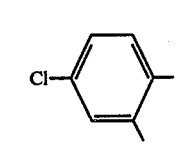 |
| n-C₃H₇ | 2,4-dichlorophenoxy 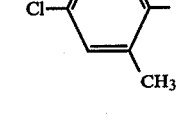 |

| R¹ | R² |
|---|---|
| n-C₃H₇ | 4-chloro-2-methylphenoxy 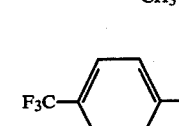 |
| n-C₃H₇ | 3-chlorophenylthio 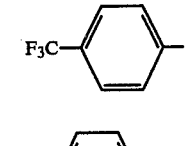 |
| n-C₃H₇ | 2-chlorophenyl 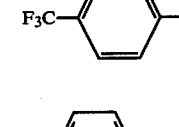 |
| n-C₃H₇ | 3,4-dichlorophenyl 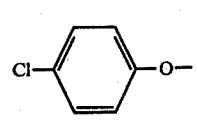 |
| n-C₃H₇ | 2,4-dichlorophenyl 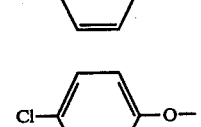 |
| n-C₃H₇ | 5-chloro-2-methylphenyl 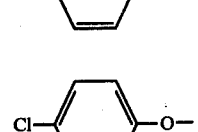 |
| n-C₃H₇ | 4-trifluoromethylphenyl 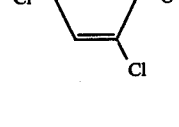 |
| i-C₃H₇ | 4-chlorophenoxy  |
| i-C₃H₇ | 2,4-dichlorophenoxy |

-continued
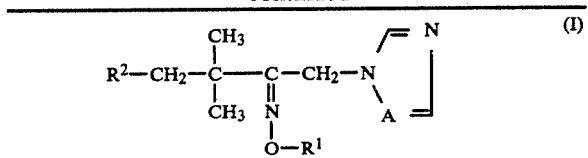
| $R^1$ | $R^2$ |
|---|---|
| i-C$_3$H$_7$ | 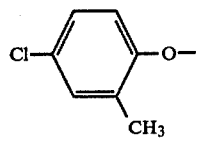 |
| i-C$_3$H$_7$ | 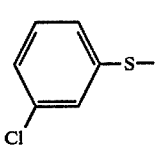 |
| i-C$_3$H$_7$ | 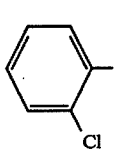 |
| i-C$_3$H$_7$ | 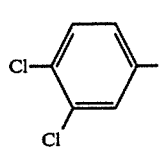 |
| i-C$_3$H$_7$ | 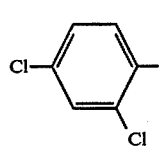 |
| i-C$_3$H$_7$ | 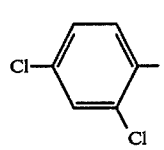 |
| i-C$_3$H$_7$ | 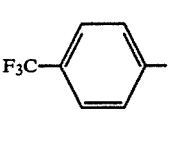 |
| n-C$_4$H$_9$ | 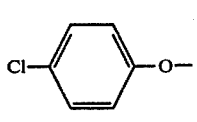 |
| n-C$_4$H$_9$ | 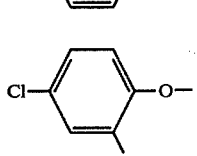 |
| n-C$_4$H$_9$ | 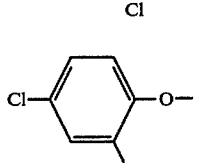 |
-continued
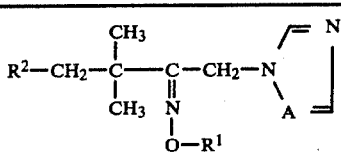
| $R^1$ | $R^2$ |
|---|---|
| n-C$_4$H$_9$ | 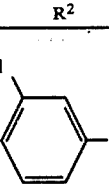 |
| n-C$_4$H$_9$ | 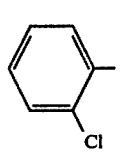 |
| n-C$_4$H$_9$ | 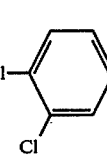 |
| n-C$_4$H$_9$ | 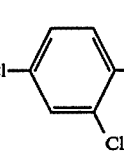 |
| n-C$_4$H$_9$ | 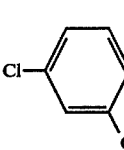 |
| n-C$_4$H$_9$ | 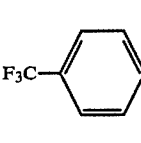 |
| i-C$_4$H$_9$ | 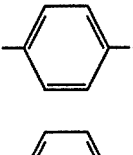 |
| i-C$_4$H$_9$ | 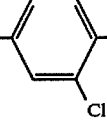 |
| i-C$_4$H$_9$ | 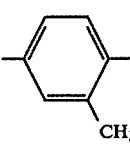 |
| i-C$_4$H$_9$ | 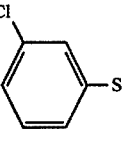 |

-continued $$\text{R}^2-\text{CH}_2-\overset{\overset{\text{CH}_3}{|}}{\underset{\underset{\text{CH}_3}{|}}{\text{C}}}-\overset{\overset{\text{N}}{\parallel}}{\underset{\underset{\text{O}-\text{R}^1}{}}{\text{C}}}-\text{CH}_2-\text{N}\overset{/\text{CH}=\text{N}\backslash}{\underset{\backslash\text{A}=/}{}}$$  (I)

| R¹ | R² |
|---|---|
| i-C₄H₉ | 2-chlorophenyl |
| i-C₄H₉ | 3,4-dichlorophenyl |
| i-C₄H₉ | 2,4-dichlorophenyl |
| i-C₄H₉ | 4-chloro-2-methylphenyl |
| i-C₄H₉ | 4-(trifluoromethyl)phenyl |
| CH₂=CH—CH₂— | 4-chlorophenoxy |
| CH₂=CH—CH₂— | 2,4-dichlorophenoxy |
| CH₂=CH—CH₂— | 4-chloro-2-methylphenoxy |
| CH₂=CH—CH₂— | 3-chlorophenylthio |

| R¹ | R² |
|---|---|
| CH₂=CH—CH₂— | 2-chlorophenyl |
| CH₂=CH—CH₂— | 3,4-dichlorophenyl |
| CH₂=CH—CH₂— | 2,4-dichlorophenyl |
| CH₂=CH—CH₂— | 4-chloro-2-methylphenyl |
| CH₂=CH—CH₂— | 4-(trifluoromethyl)phenyl |
| CH≡C—CH₂— | 4-chlorophenoxy |
| CH≡C—CH₂— | 2,4-dichlorophenoxy |
| CH≡C—CH₂— | 4-chloro-2-methylphenoxy |
| CH≡C—CH₂— | 3-chlorophenylthio |
| CH≡C—CH₂— | 2-chlorophenyl |

-continued
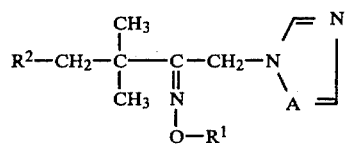 (I)
| R¹ | R² |
|---|---|
| CH≡C—CH₂— | 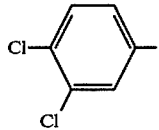 |
| CH≡C—CH₂— | 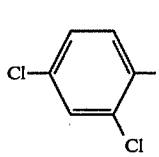 |
| CH≡C—CH₂— | 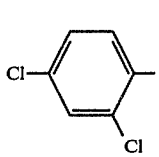 |
| CH≡C—CH₂— | 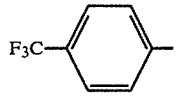 |
| 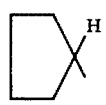 | 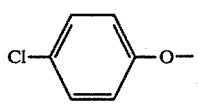 |
|  | 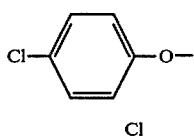 |
| 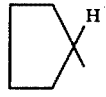 | 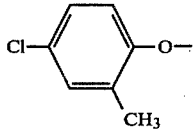 |
| 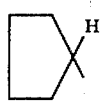 | 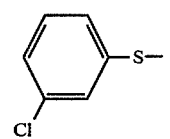 |
|  | 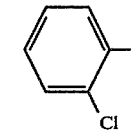 |
-continued
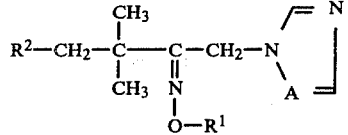 (I)
| R¹ | R² |
|---|---|
| 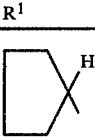 | 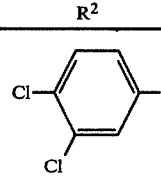 |
|  | 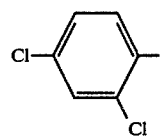 |
| 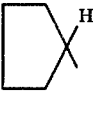 | 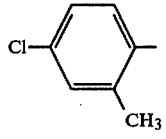 |
|  | 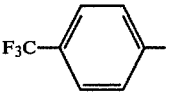 |
| CH₃—CH=CH—CH₂— | 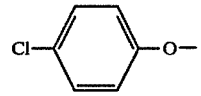 |
| CH₃—CH=CH—CH₂— | 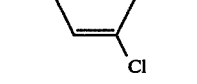 |
| CH₃—CH=CH—CH₂— | 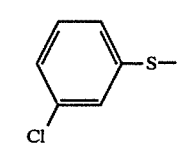 |
| CH₃—CH=CH—CH₂— | 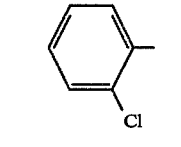 |
| CH₃—CH=CH—CH₂— | 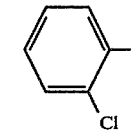 |

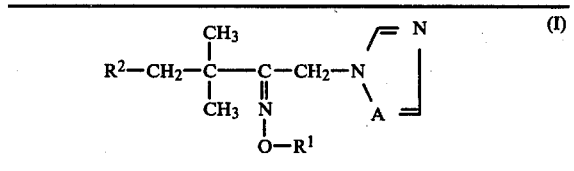

| R¹ | R² |
| --- | --- |
| CH₃—CH=CH—CH₂— | 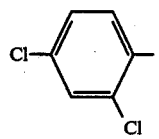 |
| CH₃—CH=CH—CH₂— | 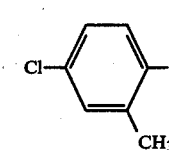 |
| CH₃—CH=CH—CH₂— | 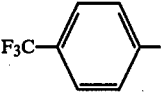 |

If, for example, 4-(4-chlorophenylsulphenyl)-3,3-dimethyl-1-(imidazol-1-yl)-butan-2-one and O-(2-butyl)-hydroxylamine are used as starting materials, the course of the reaction can be represented by the following equation (process a):

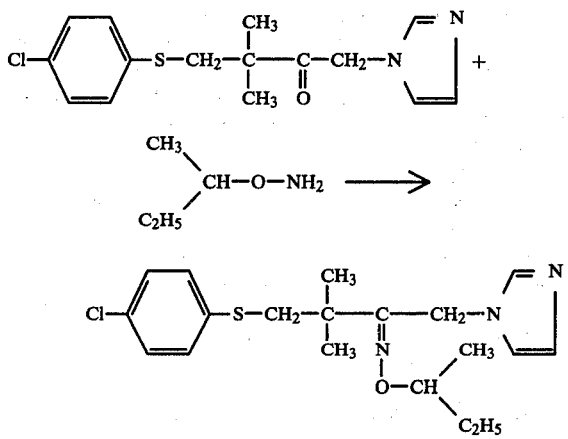

If, for example, 4-(4-chlorophenylsulphenyl)-3,3-dimethyl-1-(imidazol-1-yl)-2-oximinobutane and iodoethane are used as starting materials, the course of the reaction can be represented by the following equation (process b):

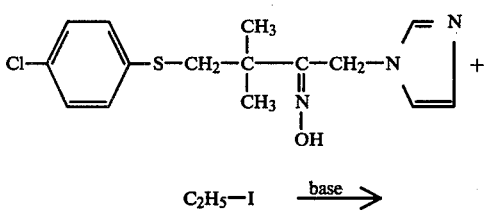

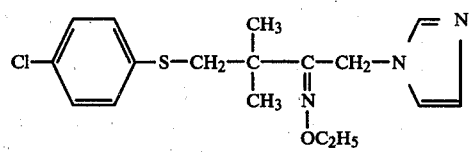

If, for example, 1-chloro-4-(4-chlorophenylsulphenyl)-3,3-dimethyl-2-methyloximinobutane and 1,2,4-triazole are used as starting materials, the course of the reaction can be represented by the following equation (process c):

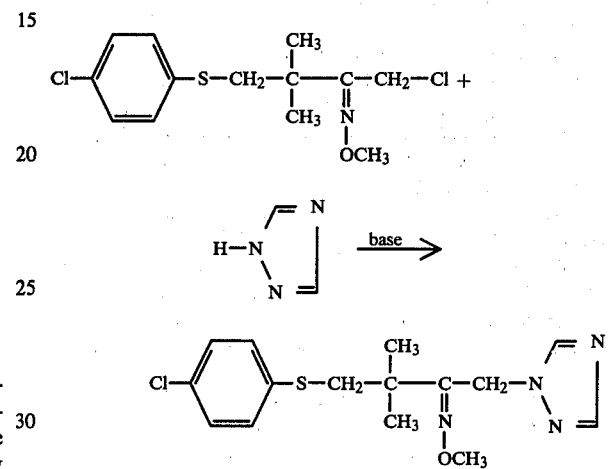

Formula (II) gives a general definition of the azolylketones which are required as starting materials in carrying out process (a) according to the invention. In this formula, A and R² preferably have those meanings which have already been mentioned, in connection with the description of the materials according to the invention of the formula (I), as preferred for these radicals.

The azolylketones of the formula (II) have not yet been disclosed. However, they are the subject of an earlier German Patent Application No. (P 3,048,266 [Le A 20 763] of Dec. 20, 1980). They can be obtained in the process given in this application by reacting 1-halogeno-2-butanones of the formula (VI)

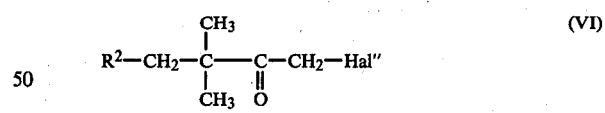

in which

R² has the abovementioned meaning and

Hal" represents chlorine or bromine, in a customary manner with 1,2,4-triazole or imidazole in the presence of an inert organic solvent, such as, for example, dimethylformamide, and in the presence of an acid-binding agent, such as, for example, potassium carbonate, at temperatures between 40° C. and 120° C.

Formula (III) gives a general definition of the optionally substituted hydroxylamines which are also required as starting materials for process (a) according to the invention. In this formula, R¹ preferably represents those radicals which have already been mentioned, in connection with the description of the materials according to the invention of the formula (I), as preferred for these substituents.

The optionally substituted hydroxylamines of the formula (III) are generally known compounds of organic chemistry.

Formula (Ia) gives a general definition of the 1-azolyl-2-oximinobutane derivatives which are required as starting materials in carrying out process (b) according to the invention. In this formula, $R^2$ and A have those meanings which have already been mentioned, in connection with the description of the materials according to the invention of the formula (I), as preferred for these radicals. The compounds of the formula (Ia) are materials according to the invention and are prepared using process (a) according to the invention.

Formula (IV) gives a general definition of the halides which are also required as starting materials for process (b) according to the invention. In this formula, $R^1$ preferably represents those radicals which have already been mentioned, in connection with the description of the materials according to the invention of the formula (I), as preferred for these substituents. Hal preferably represents chlorine or bromine.

The halides of the formula (IV) are generally known compounds of organic chemistry.

Formula (V) gives a general definition of the 1-halogeno-2-oximinobutane derivatives which are required as starting materials in carrying out process (c) according to the invention. In this formula, $R^1$ and $R^2$ preferably represent those radicals which have already been mentioned, in connection with the description of the materials according to the invention of the formula (I), as preferred for these substituents.

The 1-halogeno-2-oximinobutane derivatives of the formula (V) have not yet been disclosed. However, they can be obtained in a generally known manner by reacting 1-halogeno-2-butanones of the formula (VI) with optionally substituted hydroxylamines of the formula (III) in the presence of a solvent, preferably an alcohol, at 50° C. to 100° C., the optionally substituted hydroxylamines preferably being employed in the form of hydrochlorides in the presence of an acid-binding agent.

Alcohols and water, or mixtures of both, are preferable diluents for process (a) according to the invention.

In process (a), the reaction temperatures can be varied within a relatively wide range. In general, the reaction is carried out between 20° C. and 120° C., preferably between 50° C. and 100° C.

In carrying out process (a) according to the invention, 1 to 1.3 mols of hydroxylamine of the formula (III) are preferably used per mol of azolylketone of the formula (II). The compounds of the formula (I) are isolated by customary methods.

In a preferred embodiment of process (a), the hydroxylamines of the formula (III) are used in the form of their salts, in particular as hydrochlorides, if appropriate in the presence of an acid-binding agent, such as, for example, sodium acetate (compare also the preparation examples).

Inert organic solvents are suitable diluents for the reaction according to the invention in accordance with process (b). These preferably include ethers, such as tetrahydrofuran and dioxane, aromatic hydrocarbons, such as toluene and benzene, in individual cases also chlorinated hydrocarbons such as chloroform, methylene chloride or carbon tetrachloride, and hexamethylphosphoric triamide, acid amides, such as dimethylformamide, and sulphoxides, such as dimethyl sulphoxide.

The reaction according to the invention in accordance with process (b) is carried out, if appropriate, in the presence of a strong base. These preferably include alkali metal amides, alkali metal hydrides, alkali metal hydroxides and alkali metal carbonates, such as, for example, sodium amide, sodium carbonate, sodium hydroxide or sodium hydride and potassium amide, potassium carbonate, potassium hydroxide or potassium hydride, and quaternary ammonium hydroxides and phosphonium hydroxides, such as, for example, tetramethylammonium hydroxide, benzyltrimethylammonium hydroxide or dibenzyldimethyl ammonium hydroxide and tetraphenylphosphonium hydroxide or methyltriphenylphosphonium hydroxide.

In process (b), the reaction temperatures can be varied to within a relatively wide range. In general, the reaction is carried out between 20° C. and 150° C., preferably at room temperature. In individual cases it is advantageous to carry out the reaction at the boiling point of the solvent, for example between 60° C. and 100° C.

In carrying out process (b) according to the invention, 1 to 3 mols of halide of the formula (IV) are preferably used per mol of oxime of the formula (Ia). To isolate the final product, solvent is removed from the reaction mixture, and water and an organic solvent are added to the residue. The organic phase is separated off, worked up and purified, the latter two steps being carried out in a customary manner.

In a preferred embodiment of process (b), the reaction according to the invention is carried out in a two-phase system, such as, for example, aqueous sodium hydroxide solution or potassium hydroxide solution/toluene or methylene chloride, with the addition of 0.01 to 1 mol of a phase-transfer catalyst, such as, for example, ammonium compounds or phosphonium compounds, the ethylates being formed in the organic phase or at the phase boundary and being reacted with the halides present in the organic phase.

Inert organic solvents are preferred diluents for the reaction according to the invention in accordance with process (c). These include nitriles, such as acetonitrile, alcohols, such as ethanol, ethers, such as tetrahydrofuran or dioxane, aromatic hydrocarbons, such as toluene and benzene, formamides, such as dimethylformamide, and halogenated hydrocarbons, such as methylene chloride, carbon tetrachloride or chloroform.

The reaction according to the invention in accordance with process (c) is carried out in the presence of an acid-binding agent. All inorganic or organic acid-binding agents which can be used in a customary manner can be added, such as alkali metal carbonates, for example sodium carbonate and potassium carbonate, or such as lower tertiary alkylamines, cycloalkylamines or aralkylamines, for example triethylamine, N,N-dimethylcyclohexylamine and N,N-dimethylbenzylamine. It is also possible to use an appropriate excess of 1,2,4-triazole or imidazole.

In process (c), the reaction temperatures can be varied within a relatively wide range. In general, the reaction is carried out between 0° C. and 150° C., preferably between 60° C. and 120° C.

To carry out process (c) according to the invention, 1 to 2 mols of 1,2,4-triazole or imidazole and 1 to 2 mols of acid-binding agent are preferably used per mol of the compounds of the formula (V). The compounds of the formula (I) are isolated by customary methods.

In a particular embodiment of process (c), a procedure can be followed in which the intermediate products of the formula (V) are prepared first and the further reaction is carried out without isolating them and without changing the solvent, and the final product of the formula (I) are obtained in one operation as part of a "one-vessel process".

To prepare physiologically acceptable acid addition salts of the compounds of the formula (I), the following acids are preferred: hydrohalic acids, such as, for example, hydrochloric acid and hydrobromic acid, in particular hydrochloric acid, furthermore phosphoric acid, nitric acid, sulphuric acid, monofunctional and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as, for example, p-toluenesulphonic acid and 1,5-naphthalenedisulphonic acid.

The acid addition salts of the compounds of the formula (I) can be obtained in a simple manner by customary salt formation methods, for example by dissolving a compound of the formula (I) in a suitable organic solvent and adding the acid, for example hydrochloric acid, and isolate it in a known manner, for example by filtration, and, if necessary, purify it by washing in an inert organic solvent.

To prepare metal salt complexes of the compounds of the formula (I), salts of metals of main groups II to IV and of subgroups IV to VIII are preferred, examples which may be mentioned being copper, zinc, manganese, magnesium, tin, iron and nickel.

Possible anions of the salts are those which are preferably derived from the following acids: hydrohalic acids, such as, for example, hydrochloric acid and hydrobromic acid, furthermore phosphoric acid, nitric acid and sulphuric acid.

The metal complexes of compounds of the formula (I) can be obtained in a simple manner by customary methods, thus, for example, by dissolving the metal salt in alcohol, such as, for example, ethanol, and adding the solution to the compound of the formula (I). The metal salt complexes can be purified in a known manner, for example by filtration, isolation and, if necessary, by recrystallization.

The active compounds according to the invention exhibit a powerful microbial action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating cereal diseases, such as, for example, against the powdery mildew of barley causative organism (*Erysiphe graminis*), or against the strip disease causative organism (*Drechslera graminea*), or against the *Pyrenophora teres* and *Cochliobolus sativus* causative organism, for combating rice diseases, such as, for example, *Pyricularia oryzae* or *Pellicularia sasakii*, and for combating Venturi species, such as, for example, against the apple scab causative organism (*Venturia inaequalis*).

The active compounds which can be used according to the invention engage in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the crop plants in the particular manner desired.

Plant growth regulating compounds can be employed, for example, to inhibit vegetative growth of the plants. Such inhibition of growth is inter alia of economic interest in the case of grasses, since it is thereby possible to reduce the frequency of cutting the grass in ornamental gardens, parks and sportsgrounds, at verges, at airports or in fruit orchards. The inhibition of growth of herbaceous and woody plants at verges and in the vicinity of pipelines or overland lines or, quite generally, in areas in which heavy additional growth of plants is undesired, is also of importance.

The use of growth regulators to inhibit the growth in length of cereals is also important. The danger of lodging of the plants before harvesting is thereby reduced or completely eliminated. Furthermore, growth regulators can strengthen the stem of cereals, which again counteracts lodging. Use of growth regulators for shortening and strengthening the stem enables higher amounts of fertiliser to be applied to increase the yield, without danger of the cereal lodging.

In the case of many crop plants, inhibition of the vegetative growth makes denser planting possible, so that greater yields per area of ground can be achieved. An advantage of the smaller plants thus produced is also that the crop can be worked and harvested more easily.

Inhibition of the vegetative growth of plants can also lead to increases in yield, since the nutrients and assimilates benefit blossoming and fruit formation to a greater extent than they benefit the vegetative parts of plants.

Promotion of vegetative growth can also frequently be achieved with growth regulators. This is of great utility if it is the vegetative parts of the plants which are harvested. Promoting the vegetative growth can, however, also simultaneously lead to a promotion of generative growth, since more assimilates are formed, so that more fruit, or larger fruit, is obtained.

Increases in yield can in some cases be achieved by affecting the plant metabolism, without noticeable changes in vegetative growth. A change in the composition of plants, which in turn can lead to a better quality of the harvested products, can furthermore be achieved with growth regulators. Thus it is possible, for example, to increase the content of sugar in sugar beet, sugar cane, pineapples and citrus fruit or to increase the protein content in soybeans or cereals. Using growth regulators it is also possible, for example, to inhibit the degradation of desired constituents, such as, for example, sugar in sugar beet or sugar cane, before or after harvesting. It is also possible favourably to influence the production or the efflux of secondary plant constituents. The stimulation of latex flux in rubber trees may be mentioned as an example.

Parthenocarpous fruit can be formed under the influence of growth regulators. Furthermore, the gender of the flowers can be influenced. Sterility of the pollen can also be produced, which is of great importance in the breeding and preparation of hybrid seed.

Branching of plants can be controlled by using growth regulators. On the one hand, by breaking the apical dominance the development of side shoots can be promoted, which can be very desirable, especially in the cultivation of ornamental plants, also in connection with growth inhibition. On the other hand, however, it is also possible to inhibit the growth of side shoots. There is great interest in this action, for example, in the cultivation of tobacco or in the planting of tomatoes.

The amount of leaf on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The shedding of fruit can also be controlled with growth regulators. On the one hand, it is possible to prevent premature shedding of fruit. However, on the other hand, shedding of fruit, or even the fall of blossom, can be promoted up to a certain degree (thinning out) in order to interrupt the alternance. By alternance there is understood the peculiarity of some varieties of fruit to produce very different yields from year to year, for endogenic reasons. Finally, using growth regulators it is possible to reduce the force required to detach the fruit at harvest time so as to permit mechanical harvesting or facilitate manual harvesting.

Using growth regulators, it is furthermore possible to achieve an acceleration or retardation of ripening of the harvest product, before or after harvesting. This is of particular advantage, since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators, it is furthermore possible to influence the latent period of seeds or buds of plants, so that the plants, such as, for example, pineapple or ornamental plants in nurseries, germinate, shoot or blossom at a time at which they normally show no readiness to do so. Retarding the shooting of buds or the germination of seeds with the aid of growth regulators can be desirable in regions where frost is a hazard, in order to avoid damage by late frosts.

Finally, the resistance of plants to frost, drought or a high salt content in the soil can be induced with growth regulators. Cultivation of plants in regions which are usually unsuitable for this purpose thereby becomes possible.

The active compounds can be converted to the customary formulations, such as solutions, emulsions, suspensions, powders, foams, pastes, granules, aerosols, very fine capsules in polymeric substances and in coating compositions for seed, as well as ULV formulations.

These formulations are produced in known manner, for example by mixing the active compounds with extenders, that is liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water. By liquefying gaseous extenders or carriers are meant liquids which are gaseous at normal temperatures and under normal pressure, for example aerosol propellant, such as halogenated hydrocarbons, as well as butane, propane, nitrogen and carbon dioxide. As solid carriers there are suitable: for example, ground natural minerals, such as kaolins, clays, talc, chalk, quartz, attapulgite, montmorillonite or diatomaceous earth, and ground synthetic materials, such as highly dispersed silicic acid, alumina and silicates. As solid carriers for granules there are suitable: for example, crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example, non-ionic and anionic emulsifiers, such as polyoxyethylene-fatty acid esters, polyoxyethylene-fatty alcohol ethers, for example alkylaryl polyglycol ethers, alkylsulphonates, alkyl-sulphates, arylsulphonates as well as albumin hydrolisation products. As dispersing agents there are suitable: for example, ligninsulphite waste liquors and methylcellulose.

Adhesives such as carboxymethylcellulose and natural and synthetic polymers in the form of powders, granules and latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs and azo-or-metal-phthalocyanine dyestuffs, and trace nutrients such as salts of iron, manganese, boron, copper cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, and also as mixtures with fertilizers and other growth regulators.

The active compounds can be used as such, in the form of their formulations or as the use forms prepared therefrom, such as ready-to-use solutions, emulsifiable concentrates, emulsions foams, suspensions, wettable powders, pastes, soluble powders, dusting agents and granules. They are used in the customary manner, for example by watering, spraying, atomizing, scattering, dusting, foaming, coating and the like. Furthermore, it is possible to apply the active compounds in accordance with the ultra-low volume process or to inject the active compound preparation or the active compound itself into the soil. It is also possible to treat the seeds of plants.

When using the compounds according to the invention as plant growth regulators, the amounts applied can be varied within a substantial range. In general, 0.01 to 50 kg, preferably 0.05 to 10 kg, of the active compound are employed per hectare of soil surface.

When using the materials according to the invention as plant growth regulators, the rule is that the growth regulators are applied within a preferred period of time, the exact definition of which depends on the climatic and vegetative circumstances.

Also when using the materials according to the invention as fungicides, the amount used can be varied within a substantial range depending on the mode of application. In the treatment of parts of plants, the active compound concentrations in the use forms are thus, in general, between 1 and 0.0001% by weight, preferably between 0.5 and 0.001% by weight. For the treatment of seed, amounts of active compound of 0.001 and 50 g per kilogramm of seed, preferably 0.01 to 10 g, are generally required. For the treatment of soil, active compound concentrations, at the point of action, of 0.00001 to 0.1% by weight, preferably of 0.0001 to 0.02%, are required.

PREPARATION EXAMPLES

Example 1

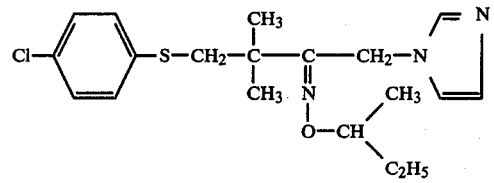

(Process a)

30.9 g (0.1 mol) of 4-(4-chlorophenylsulphenyl)-3,3-dimethyl-1-(imidazol-1-yl)-butan-2-one are refluxed for 20 hours in 600 ml of toluene under a water separator together with 11.6 g (0.13 mol) of 0-(2-butyl)-hydroxylamine and 2 g of p-toluenesulphonic acid. The reaction mixture is cooled down, washed with water, dried over sodium sulphate, and concentrated in vacuo. The residue is purified by column chromatography.

10.6 g (28% of theory) of 2-(2-butyloximino)-4-(4-chlorophenylsulphenyl)-3,3-dimethyl-1-(imidazol-1-yl)-butane are obtained as an oil with a refractive index, $n_D^{20}$ of 1.5630.

Preparation of the starting product

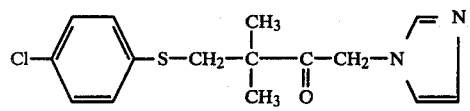

199 g (0.618 mol) of 1-bromo-4-(4-chlorophenylsulphenyl)-3,3-dimethylbutan-2-one, 120 g (1.76 mols) of imidazole and 243.5 g (1.76 mols) of potassium carbonate in 3 liters of acetone are stirred under reflux for 5 hours. The mixture is then allowed to cool, the inorganic salts are filtered off with suction, and the filtrate is concentrated. The residue is taken up in methylene chloride, washed three times with water, dried over sodium sulphate, and concentrated. Recrystallizing from diisopropyl ether produces 156 g (82% of theory) of 4-(4-chlorophenylsulphenyl)-3,3-dimethyl-1-(imidazol-1-yl)-butan-2-one having a melting point of 50° C.

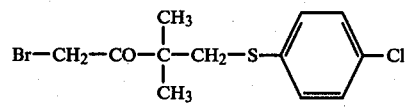

64 g (0.4 mol) of bromine are added slowly at room temperature to 97 g (0.4 mol) of 1-(4-chlorophenylsulphenyl)-2,2-dimethylbutan-3-one. The reaction mixture is worked up as in Example 1. 127 g (99% of theory) of 1-bromo-4-(4-chlorophenylsulphenyl)-3,3-dimethylbutan-2-one are obtained as a viscous oil.

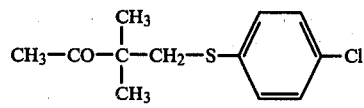

134.5 g (1 mol) of 4-chloropinacolone are stirred with 216 g (1.5 mols) of 4-chlorothiophenol and 210 g (1.52 mols) of potassium carbonate in 500 ml of dimethylformamide at 150° C. and under pressure of 2 to 4 bar for 15 hours. The mixture is allowed to cool down to room temperature and is stirred with 10 liters of water and extracted with ether. The ether phase is dried over sodium sulphate and concentrated, and the residue is distilled in vacuo. 151 g (62% of theory) of 1-(4-chlorophenylsulphenyl)-2,2-dimethylbutan-3-one having a boiling point of 146° C./0.7 mbar are obtained.

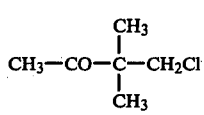

11.6 g (0.1 mol) of 2,2-dimethyl-1-hydroxybutan-3-one (for preparation see Example 3) are added dropwise to 20.5 (0.1 mol) of N,N-dimethyl-1,2,2-trichlorovinylamine at 50° to 60° C. (cooling with ice). After a stirring time of 2 hours at 60° C., the mixture is distilled under a water jet vacuum. 8.1 g (60% of theory) are obtained of 4-chloropinacolone with a boiling of 60°–62° C./16 mbar.

Example 2

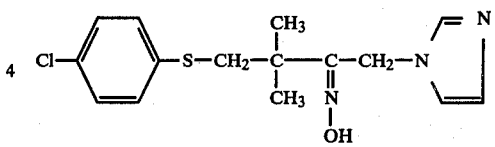

(Process a)

30.9 g (0.1 mol) of 4-(4-chlorophenylsulphenyl)-3,3-dimethyl-1-(imidazol-1-yl)-butan-2-one are refluxed for 4 hours in 200 ml of toluene under a water separator together with 20 g (0.13 mol) of hydroxylamine hydrochloride, 11.8 g (0.13 mol) of triethylamine and 2 g of p-toluenesulphonic acid. The reaction mixture is cooled down, washed with water, dried over sodium sulphate, and concentrated in vacuo. The residue is purified by column chromatography.

13.6 g (42% of theory) are obtained of 4-(4-chlorophenylsulphenyl)-3,3-dimethyl-1-(imidazol-1-yl)-2-oximinobutane with a melting point of 125°–126° C.

Example 3

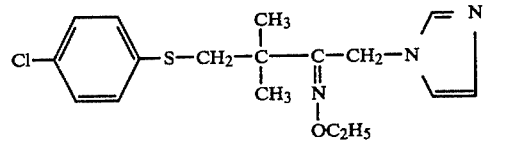

(Process b)

13.0 g (0.04 mol) of 4-(4-chlorophenylsulphenyl)-3,3-dimethyl-1-(imidazol-1-yl)-2-oximinobutane are dissolved in 50 ml of dimethylformamide, and 4.5 g (0.04 mol) of sodium t-butylate are added. After the mixture has been warmed to 50° C., 6.9 g (0.044 mol) of iodoethane are added dropwise, and the mixture is stirred for 2 hours at 50° C. The reaction mixture is cooled down, stirred with 600 ml of water, and extracted with ethyl acetate. The ethyl acetate phase is washed three times with water, dried over sodium sulphate, and concentrated in vacuo at a bath temperature of 50° C. The residue is purified by column chromatography. 12.1 g (86.4% of theory) are obtained of 4-(4-chlorophenylsulphenyl)-3,3-dimethyl-2-ethyloximino-1-imidazol-1-yl)-butane as an oil with a refractive index, $n_D^{20}$, of 1.5699.

The following compounds of the general formula (I)

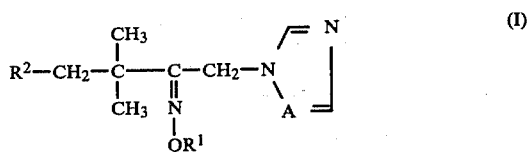

are obtained in a corresponding manner and is in the processes given:

| Example No. | $R^1$ | $R^2$ | A | Melting point (°C.) or refractive index ($n_D^{20}$) |
|---|---|---|---|---|
| 4 | $CH_3$ | Cl—〇—S— | CH | 1.5835 |
| 5 | $CH_3$ | Cl—〇—S— | CH | 118–120(× HCl) |
| 6 | $CH_3$ | Cl—〇—S— | CH | 158(× $CuCl_2$) |
| 7 | $n-C_3H_7$ | Cl—〇—S— | CH | 1.5665 |
| 8 | $i-C_3H_7$ | Cl—〇—S— | CH | 1.5632 |
| 9 | $n-C_4H_9$ | Cl—〇—S— | CH | 1.5567 |
| 10 | $n-C_7H_{15}$ | Cl—〇—S— | CH | 1.5419 |
| 11 | H | Cl—〇—S— | CH | 1.5730 |
| 12 | H | Cl—〇—S— | CH | 1.5522 |
| 13 | $CH_2=CH-CH_2-$ | Cl—〇—S— | CH | 1.5790 |
| 14 | $HC\equiv C-CH_2-$ | Cl—〇—S— | CH | 1.5849 |
| 15 | $CH_3-CH=CH-CH_2-$ | Cl—〇—S— | CH | 1.5722 |

-continued

| Example No. | R¹ | R² | A | Melting point (°C.) or refractive index ($n_D^{20}$). |
|---|---|---|---|---|
| 16 | 2,6-Cl₂-C₆H₃-CH₂- | 4-Cl-C₆H₄-S- | CH | 1.5997 |
| 17 | H | 4-Cl-C₆H₄-O- | CH | 175–176(× HCl) |
| 18 | C₂H₅ | 4-Cl-C₆H₄- | CH | 1.5454 |
| 19 | n-C₃H₇ | 4-Cl-C₆H₄- | CH | 1.5431 |
| 20 | n-C₄H₉ | 4-Cl-C₆H₄- | CH | 1.5400 |
| 21 | CH₃ | 4-Cl-C₆H₄-S- | N | 1.5776 |
| 22 | sec.-C₄H₉ | 4-Cl-C₆H₄-S- | N | 1.5523 (form A)* |
| 23 | sec.-C₄H₉ | 4-Cl-C₆H₄-S- | N | 1.5496 (form B)* |
| 24 | n-C₇H₁₅ | 4-Cl-C₆H₄-S- | N | 1.5334 |
| 25 | cyclobutyl | 4-Cl-C₆H₄-S- | N | 1.5673 |
| 26 | 2,4-Cl₂-C₆H₃-CH₂- | 4-Cl-C₆H₄-S- | N | 1.5961 |
| 27 | 2,6-Cl₂-C₆H₃-CH₂- | 4-Cl-C₆H₄-S- | N | 1.5850 |
| 28 | n-C₄H₉ | 4-Cl-C₆H₄-O- | N | 1.5170 |
| 29 | 2,6-Cl₂-C₆H₃-CH₂- | 4-Cl-C₆H₄-O- | N | 165–170(× HCl) |
| 30 | 3-CH₃O-C₆H₄-CH₂- | 4-Cl-C₆H₄-O- | N | 114(× HCl) |
| 31 | n-C₃H₇ | 4-Cl-C₆H₄- | N | 42 |
| 32 | i-C₃H₇ | 4-Cl-C₆H₄- | N | 66 |

-continued

| Example No. | R¹ | R² | A | Melting point (°C.) or refractive index ($n_D^{20}$) |
|---|---|---|---|---|
| 33 | n-C₇H₁₅ | 4-Cl-C₆H₄- | N | 1.5185 |
| 34 | 2,6-Cl₂-C₆H₃-CH₂- | 4-Cl-C₆H₄- | N | 1.5779 |
| 35 | 2,6-Cl₂-C₆H₃-CH₂- | C₆H₅- | N | 1.5610 |
| 36 | sec.-C₄H₉ | 4-Cl-C₆H₄-S- | N | 1.5496 |
| 37 | H | 4-Br-C₆H₁₀-O- | N | F 168°–190° C. (× HCl) |
| 38 | H | 4-Br-C₆H₄-O- | CH | F 98°–100° C. |
| 39 | H | 3-CH₃-4-Cl-C₆H₃-O- | N | F 93°–95° C. |
| 40 | n-C₄H₉ | 4-Br-C₆H₄-O- | N | $n_D^{25}$ 1.5363 |
| 41 | CH₃ | 4-Cl-C₆H₄- | CH | viscous oil |
| 42 | n-C₃H₇- | 4-Cl-C₆H₄-O- | N | 1.5234 |
| 43 | CH₃-CH=CH-CH₂- | 4-Cl-C₆H₄-O- | N | 1.5205 |
| 44 | CH₃-CH=CH-CH₂- | 3,4-Cl₂-C₆H₃-O- | N | 1.5379 |
| 45 | CH₂=CH-CH₂- | 3,4-Cl₂-C₆H₃-O- | N | 1.5325 |
| 46 | C₂H₅- | 3,4-Cl₂-C₆H₃-O- | N | 1.5353 |
| 47 | C₂H₅- | 4-Cl-C₆H₄-O- | N | 1.5329 |
| 48 | n-C₃H₇- | 3,4-Cl₂-C₆H₃-O- | N | 1.5264 |

-continued

| Example No. | R[1] | R[2] | A | Melting point (°C.) or refractive index ($n_D^{20}$) |
|---|---|---|---|---|
| 49 | n-C$_4$H$_9$— | Cl—C$_6$H$_3$(CH$_3$)—O— | N | 1.5262 |
| 50 | H | Cl—C$_6$H$_3$(CH$_3$)—O— | N | 208(× HCl) |
| 51 | CH$_2$=CH—CH$_2$— | Cl—C$_6$H$_4$—O— | N | $n_D^{22} = 1.5352$ |
| 52 | n-C$_4$H$_9$— | Cl—C$_6$H$_3$(CH$_3$)—O— | N | $n_D^{20.8} = 1.5208$ |
| 53 | C$_2$H$_5$ | Cl—C$_6$H$_3$(CH$_3$)—O— | N | $n_D^{20.7} = 1.5278$ |
| 54 | H | Cl—C$_6$H$_4$— | CH | 153 |
| 55 | HC≡C—CH$_2$— | Cl—C$_6$H$_4$— | CH | 1.5574 |
| 56 | CH$_3$—CH=CH—CH$_2$— | Cl—C$_6$H$_4$— | CH | 1.5493 |
| 57 | H | Cl—C$_6$H$_4$— | N | 135–138 |
| 58 | HC≡C—CH$_2$— | Cl—C$_6$H$_4$— | N | 1.5511 |
| 59 | CH$_2$=CH—CH$_2$— | Cl—C$_6$H$_4$— | N | 1.5431 |
| 60 | H | F—C$_6$H$_4$— | CH | 145 |
| 61 | CH$_3$ | F—C$_6$H$_4$— | CH | 1.5365 |
| 62 | n-C$_4$H$_9$ | Cl—C$_6$H$_4$—O— | CH | $n_D^{21.8} = 1.5270$ |

*forms A and B: the two possible geometric isomers.

USE EXAMPLES

In the following use examples, the compounds given below are used as comparative substances:

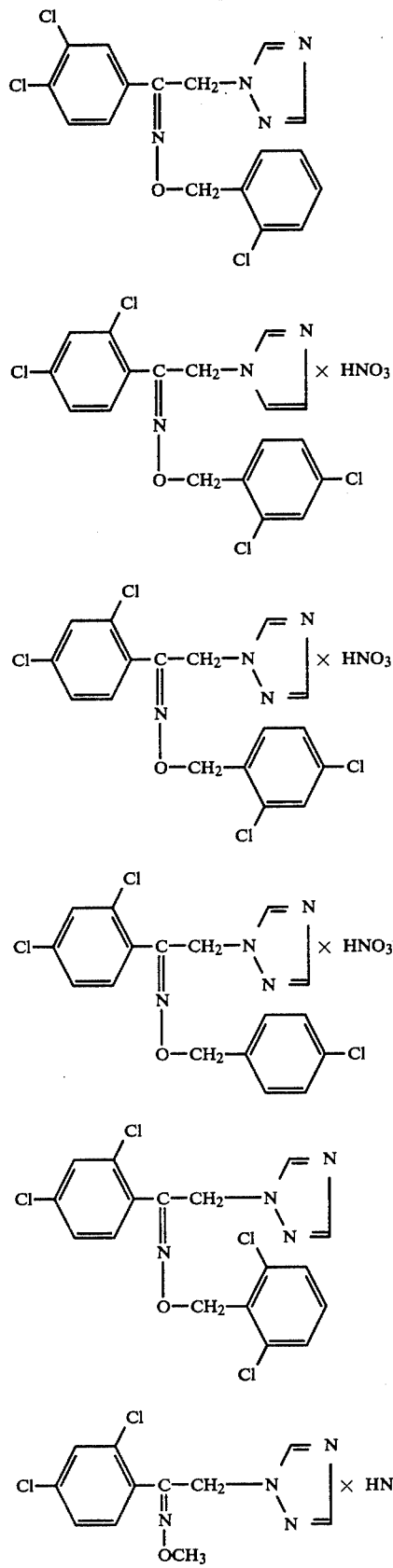

EXAMPLE A
Erysiphe test (barley)/protective

Solvent: 100 parts by weight of dimethylformamide
Emulsifier: 0.25 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dewmoist. After the spray coating has dried on, the plants are dusted with spores of Erysiphe graminis f.sp. hordei.

The plants are placed in a greenhouse at a temperature of about 20° C. and a relative atmospheric humidity of about 80%, in order to promote the development of powdery mildew pustules.

Evaluation is carried out 7 days after the inoculation.

In this test, a clearly superior activity is shown, compared with the prior art, for example by the compounds according to the following preparation examples: 8, 9, 11, 12, 16, 17, 22, 23, 24, 25, 26, 27, 28 and 30.

EXAMPLE B
Pyricularia test (rice)/protective

Solvent: 12.5 parts by weight of acetone
Emulsifier: 0.3 part by weight of alkylaryl polyglycol ether To produce a suitable preparation of active compound, 1 part by weight of active compound is mixed with the stated amount of solvent and the concentrate is diluted with water and the given amount of emulsifier, to the desired concentration.

To test for protective activity, young rice plants are sprayed with the preparation of active compound until dripping wet. After the spray coating has dried on, the plants are inoculated with an aqueous spore suspension of Pyricularia oryzae. The plants are then placed in a greenhouse at 100% relative atmospheric humidity and 25° C.

Evaluation of attack by the disease is carried out 4 days after the inoculation.

In this test, a clearly superior activity is shown, compared with the prior art, for example by the compounds according to the following preparation examples: 7 and 23.

EXAMPLE C
Pellicularia test (rice)

Solvent: 12.5 parts by weight of acetone
Emulsifier: 0.3 part by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for activity, young rice plants in the 3 to 4 leaf stage are sprayed until dripping wet. The plants remain in a greenhouse until they have dried off. The plants are then inoculated with Pellicularia sasakii and are placed at 25° C. and 100% relative atmospheric humidity.

The evaluation of the disease infestation is carried out 5-8 days after the inoculation.

In this test, a clearly superior activity compared with the prior art is shown, for example, by the compound according to the following preparation example: 7.

EXAMPLE D

*Drechslera graminea* test (barley)/seed treatment (syn. *Helminthosporium gramineum*)

The active compounds are used as dry dressings. These are prepared by extending the particular active compound with a ground mineral to give a finely pulverulent mixture, which ensures uniform distribution on the seed surface.

To apply the dressing, the infected seed is shaken with the dressing in a closed glass flask for 3 minutes.

The seed is embedded in sieved, moist standard soil and is exposed to a temperature of 4° C. in closed Petri dishes in a refrigerator for 10 days. Germination of the barley, and possibly also of the fungus spores, is thereby initiated. 2 batches of 50 grains of the pregerminated barley are subsequently sown 3 cm deep in standard soil and are cultivated in a greenhouse at a temperature of about 18° C., in seedboxes which are exposed to light for 15 hours daily.

About 3 weeks after sowing, the plants are evaluated for symptoms of stripe disease.

In this test, a clearly superior activity compared with the prior art is shown, for example, by the compound according to the following preparation example: 17.

EXAMPLE E

Inhibition of growth of cotton
Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Cotton plants are grown in a greenhouse until the 5th foliage leaf has unfolded completely. In this stage, the plants are sprayed with the preparations of active compound until dripping wet. After 3 weeks, the additional growth of the plants is measured and the inhibition of growth is calculated as a percentage of the additional growth of the control plants. 100% inhibition of growth means growth has stopped and 0% means growth corresponds to the control plants.

In this test, the active compounds according to examples 22, 25, 31, 32 and 33 show a clearly superior activity compared with the prior art.

EXAMPLE F

Inhibition of growth of soybeans
Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Soybean plants are grown in a greenhouse until the first secondary leaf has unfolded completely. In this stage, the plants are sprayed with the preparation of active compound until dripping wet. After 3 weeks, the additional growth is measured for all plants and the inhibition of growth is calculated as a percentage of the additional growth of the control plants. 100% inhibition of growth means growth has stopped and 0% means growth corresponds to the control plants.

In this test, the active compounds according to examples 22, 25, 28, 31 and 32 show good influence on growth compared to the control.

EXAMPLE G

Inhibition of growth of sugar beet
Solvent: 30 parts by weight of dimethylformamide
Emulsifier: 1 part by weight of polyoxyethylene sorbitan monolaurate.

To produce a suitable preparation of active compound, 1 part by weight of active compound is mixed with the stated amounts of solvent and emulsifier and the mixture is made up to the desired concentration with water.

Sugar beet is grown in a greenhouse until formation of the cotyledons is complete. In this stage, the plants are sprayed with the preparation of active compound until dripping wet. After 14 days, the additional growth of the plants is measured and the inhibition of growth is calculated as a percentage of the additional growth of the control plants. 0% inhibition of growth means growth corresponding to that of the control plants. Negative values characterize inhibition of growth whereas positive values characterize promotion of growth compared to the control plants.

In this test, the active compounds according to examples 22, 23, 24, 25, 31 and 32 show considerable inhibition of growth.

EXAMPLE H

Simulation of assimilation of $CO_2$ in soybeans
Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Soybean plants are grown in a greenhouse until the first secondary leaf is unfolded completely. In this stage, the plants are sprayed with the preparations of active compound until dripping wet. In the further course of the experiment the $CO_2$ assimilation of the plants is measured by customary methods. The values are compared with those of control plants not treated with the active compounds.

In this test, the active compound according to example 28 showed a good activity compared to the control.

It will be appreciated that the instant specification and examples are set forth by way of illustration and not limitation, and that various modifications and changes may be made without departing from the spirit and scope of the present invention.

We claim:

1. A 1-azolyl-2-oximinobutane derivative of the formula $$R^2-CH_2-\underset{\underset{CH_3}{|}}{\overset{\overset{CH_3}{|}}{C}}-\underset{\underset{\underset{C-R^1}{|}}{N}}{\overset{\|}{C}}-CH_2-N\begin{pmatrix}=N\\ \\A\end{pmatrix}$$

in which
A is nitrogen or CH, $R^1$ is hydrogen, alkyl, halogenoalkyl, alkenyl, alkinyl, or optionally substituted benzyl, phenyl, cycloalkyl, cycloalkylalkyl or cycloalkenyl, and $R^2$ is optionally substituted phenyl, phenoxy, phenylthio, phenylsulphinyl or phenylsulphonyl, or a physiologically acceptable addition product thereof with an acid or metal salt.

2. A compound or addition product according to claim 1, in which $R^1$ is alkyl, alkenyl or alkinyl each having up to 8 carbon atoms, or cyclopentyl, cyclohexyl, cyclopropylmethyl, cyclopropylethyl, cyclopentylmethyl, cyclohexylmethyl, phenyl or benzyl each optionally substituted up to three times with one or more radicals selected from the group consisting of fluorine, chlorine, bromine, cyano, nitro, methyl, ethyl, methoxy, trifluoromethyl, trifluoromethoxy, and optionally fluorine- or chlorine-substituted phenyl or phenoxy, and $R^2$ is phenyl, phenoxy, phenylthio, phenylsulphinyl or phenylsulphonyl, each of which is optionally substituted up to two times with one or more radicals selected from the group consisting of fluorine, chlorine, bromine, methyl and optionally fluorine-, chlorine- or methyl-substituted phenyl or phenoxy.

3. A compound according to claim 1, wherein such compound is 2-methoximino-4-(4-chlorophenylsulphenyl)-3,3-dimethyl-1-(imidazol-1-yl)-butane of the formula

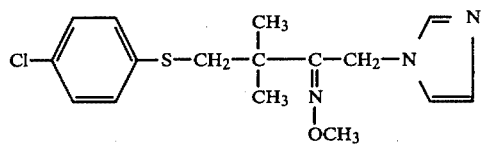

or a physiologically acceptable addition product thereof with and acid or metal salt.

4. A compound according to claim 1, wherein such compound is 2-propargoximino-4-(4-chlorophenylsulphenyl)-3,3-dimethyl-1-(imidazol-1-yl)-butane of the formula

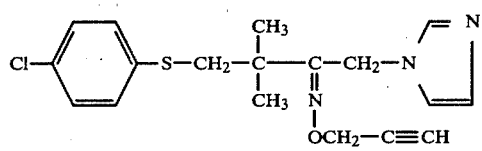

or a physiologically acceptable addition product thereof with an acid or metal salt.

5. A compound according to claim 1, wherein such compound is 2-hydroximino-4-(4-chlorophenoxy)-3,3-dimethyl-1-(imidazol-1-yl)-butane of the formula

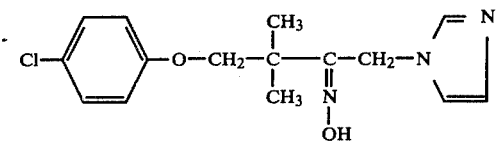

or a physiologically acceptable addition product thereof with an acid or metal salt.

6. A compound according to claim 1, wherein such compound is 2-ethoximino-4-(4-chlorophenyl)-3,3-dimethyl-1-(imidazol-1-yl)-butane of the formula

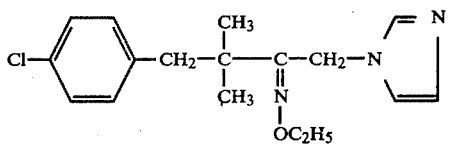

or a physiologically acceptable addition product thereof with an acid or metal salt.

7. A compound according to claim 1, wherein such compound is 2-methoximino-4-(4-chlorophenyl)-3,3-dimethyl-1-(imidazol-1-yl)-butane of the formula

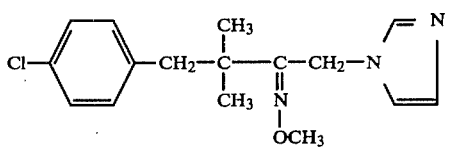

or a physiologically acceptable addition product thereof with an acid or metal salt.

8. A fungicidal or plant growth regulating composition comprising an effective amount of a compound or addition product according to claim 1 in admixture with a diluent.

9. A method of combating fungi which comprises applying to said fungi or a habitat thereof a fungicidally effective amount of a compound or addition product thereof according to claim 1.

10. The method according to claim 9, wherein such compound is 2-methoximino-4-(4-chlorophenylsulphenyl)-3,3-dimethyl-1-imidazol-1-yl)-butane, 2-proparagoximino-4-(chlorophenylsulphenyl)-3,-dimethyl-1-(imidazol-1-yl)-butane, 2-hydroximino-4-(chlorophenoxy)-3,3-dimethyl-1-(imidazol-1-yl)-butane, 2-ethoximino-4-(4-chlorophenyl)-3,3-dimethyl-1-imidazol-1-yl)-butane or 2-methoximino-4-(4-chlorophenyl)-3,3-dimethyl-1-(imidazol-1-yl)-butane or a physiologically acceptable addition product thereof with an acid or metal salt.

* * * * *